United States Patent
Grosfils et al.

(10) Patent No.: US 11,065,180 B2
(45) Date of Patent: Jul. 20, 2021

(54) SYSTEMS AND METHODS FOR IDENTIFYING MEDICINES DEPOSITED IN A COMPARTMENT OF A PILL BOX ACCORDING TO A PRESCRIPTION

(71) Applicant: Matthieu Grosfils, Montréal (CA)

(72) Inventors: Matthieu Grosfils, Montréal (CA); Jean-Pierre Forté, Longueuil (CA)

(73) Assignee: Matthieu Grosfils, Montréal (CA)

( * ) Notice: Subject to any disclaimer, the term of this patent is extended or adjusted under 35 U.S.C. 154(b) by 278 days.

(21) Appl. No.: 16/312,981

(22) PCT Filed: Jun. 22, 2017

(86) PCT No.: PCT/CA2017/050763
§ 371 (c)(1),
(2) Date: May 10, 2019

(87) PCT Pub. No.: WO2017/219144
PCT Pub. Date: Dec. 28, 2017

(65) Prior Publication Data
US 2019/0269576 A1 Sep. 5, 2019

(30) Foreign Application Priority Data
Jun. 23, 2016 (CA) .................................. CA2933860

(51) Int. Cl.
*A61J 7/00* (2006.01)
*G07F 17/00* (2006.01)
(Continued)

(52) U.S. Cl.
CPC ............. *A61J 1/035* (2013.01); *A61J 7/0084* (2013.01); *A61J 7/02* (2013.01); *A61J 7/0454* (2015.05);
(Continued)

(58) Field of Classification Search
CPC ........ A61J 1/035; A61J 7/0454; A61J 7/0084; A61J 7/02; A61J 7/0069; G01N 21/9508;
(Continued)

(56) References Cited

U.S. PATENT DOCUMENTS 2,940,355 A  6/1960 Cary
4,812,904 A  3/1989 Maring et al.
(Continued)

FOREIGN PATENT DOCUMENTS

CA  2217220  6/1998
WO  0225568  3/2002
(Continued)

OTHER PUBLICATIONS

English Translation—Machine Translation of JPWO20151707762, "Drug Sorting Device", published on Apr. 20, 2017.

*Primary Examiner* — Michael Collins
(74) *Attorney, Agent, or Firm* — Bereskin & Parr LLP/S.E.N.C.R.L., s.r.l.

(57) ABSTRACT

The disclosure relates to a system for identifying medicines, comprising a first measurement device for identifying, from the top, at least one first medicine deposited in a compartment of a pill box and analysing at least one identifying characteristic of the first medicine; and a second measurement device for identifying, from the bottom, at least one second medicine deposited in the compartment of said pill box and analysing at least one identifying characteristic of the second medicine. The system comprises a device for comparing the characteristic of the first medicine and the characteristic of the second medicine, for determining at least one validated medicine and comparing the characteristic of the validated medicine with medicine signature characteristics. The system also comprises a validation device for obtaining an identified content for the compartment and comparing the identified content with a prescrip- (Continued)

tion. Methods for identifying and validating medicines are also disclosed.

8 Claims, 10 Drawing Sheets

(51) Int. Cl.
| | |
|---|---|
| A61J 7/04 | (2006.01) |
| G01N 21/95 | (2006.01) |
| A61J 1/03 | (2006.01) |
| A61J 7/02 | (2006.01) |
| G16H 20/13 | (2018.01) |
| G06Q 10/08 | (2012.01) |
| B65B 57/18 | (2006.01) |
| G01N 21/31 | (2006.01) |
| B65B 57/00 | (2006.01) |
| B65B 5/10 | (2006.01) |
| G01N 21/65 | (2006.01) |
| G01N 21/64 | (2006.01) |
| G01N 21/3563 | (2014.01) |

(52) U.S. Cl.
CPC .............. *B65B 57/00* (2013.01); *B65B 57/18* (2013.01); *G01N 21/31* (2013.01); *G01N 21/9508* (2013.01); *G06Q 10/087* (2013.01); *G07F 17/0092* (2013.01); *G16H 20/13* (2018.01); *A61J 7/0069* (2013.01); *B65B 5/103* (2013.01); *G01N 21/3563* (2013.01); *G01N 21/6456* (2013.01); *G01N 21/65* (2013.01); *G01N 2021/6423* (2013.01)

(58) Field of Classification Search
CPC ........... G01N 21/65; G01N 2021/6423; G01N 21/6456; G01N 21/3563; G07F 17/0092; G16H 20/13; G06Q 10/087; B65B 57/00; B65B 5/103
See application file for complete search history.

(56) References Cited

U.S. PATENT DOCUMENTS

| | | | |
|---|---|---|---|
| 5,150,425 A | 9/1992 | Martin et al. | |
| 5,806,670 A | 9/1998 | Harlan et al. | |
| 6,026,189 A | 2/2000 | Greenspan | |
| 6,324,253 B1 | 11/2001 | Yuyama et al. | |
| 6,535,637 B1 | 3/2003 | Wootton et al. | |
| 7,080,755 B2 | 7/2006 | Handfield et al. | |
| 7,218,395 B2 | 5/2007 | Kaye et al. | |
| 7,828,147 B2 | 11/2010 | Caracciolo et al. | |
| 7,874,489 B2 | 1/2011 | Mercolino | |
| 8,374,965 B2 | 2/2013 | Friend et al. | |
| 8,600,548 B2 | 12/2013 | Bossi et al. | |
| 8,727,208 B2 | 5/2014 | Poisner | |
| 8,914,146 B2 * | 12/2014 | Carson | B65B 57/16 |
| | | | 700/216 |
| 9,238,518 B2 | 1/2016 | Luciano, Jr. et al. | |
| 9,299,212 B2 | 3/2016 | Amano et al. | |
| 9,313,464 B2 | 4/2016 | Pellerin et al. | |
| 9,336,552 B1 | 5/2016 | Freeman et al. | |
| 9,345,636 B2 | 5/2016 | Ahmadi | |
| 2003/0070622 A1 * | 4/2003 | Vaags | A01K 61/80 |
| | | | 119/51.11 |
| 2006/0045323 A1 | 3/2006 | Ateya | |
| 2009/0080735 A1 | 3/2009 | Chapman et al. | |
| 2010/0051644 A1 * | 3/2010 | Pluvinage | G01G 13/02 |
| | | | 222/58 |
| 2010/0284607 A1 | 11/2010 | Van Den Hengel et al. | |
| 2011/0081087 A1 | 4/2011 | Moore | |
| 2012/0083666 A1 | 4/2012 | Waugh et al. | |
| 2012/0201434 A1 | 8/2012 | Natali et al. | |
| 2013/0142406 A1 | 6/2013 | Lang et al. | |
| 2014/0113283 A1 | 4/2014 | Suh et al. | |
| 2015/0066204 A1 | 3/2015 | Patel et al. | |
| 2015/0127145 A1 | 5/2015 | Kim | |
| 2015/0302255 A1 | 10/2015 | Gershtein et al. | |
| 2015/0331887 A1 | 11/2015 | Botten | |
| 2015/0350570 A1 | 12/2015 | Helgason et al. | |
| 2016/0007138 A1 | 1/2016 | Palanisamy et al. | |
| 2016/0071318 A1 | 3/2016 | Lee et al. | |
| 2016/0073096 A1 | 3/2016 | Hillebrand et al. | |
| 2016/0085940 A1 | 3/2016 | Jacobs et al. | |
| 2016/0132660 A1 | 5/2016 | Barajas et al. | |
| 2021/0041472 A1 * | 2/2021 | Limbach | G01N 21/59 |

FOREIGN PATENT DOCUMENTS

| | | |
|---|---|---|
| WO | 2015126254 | 8/2015 |
| WO | 2015170762 | 4/2017 |

* cited by examiner

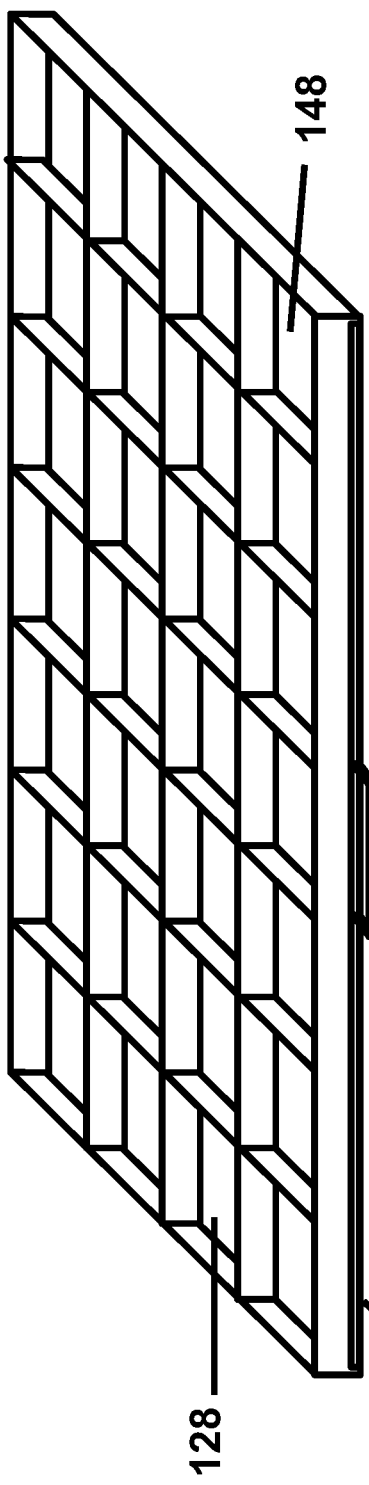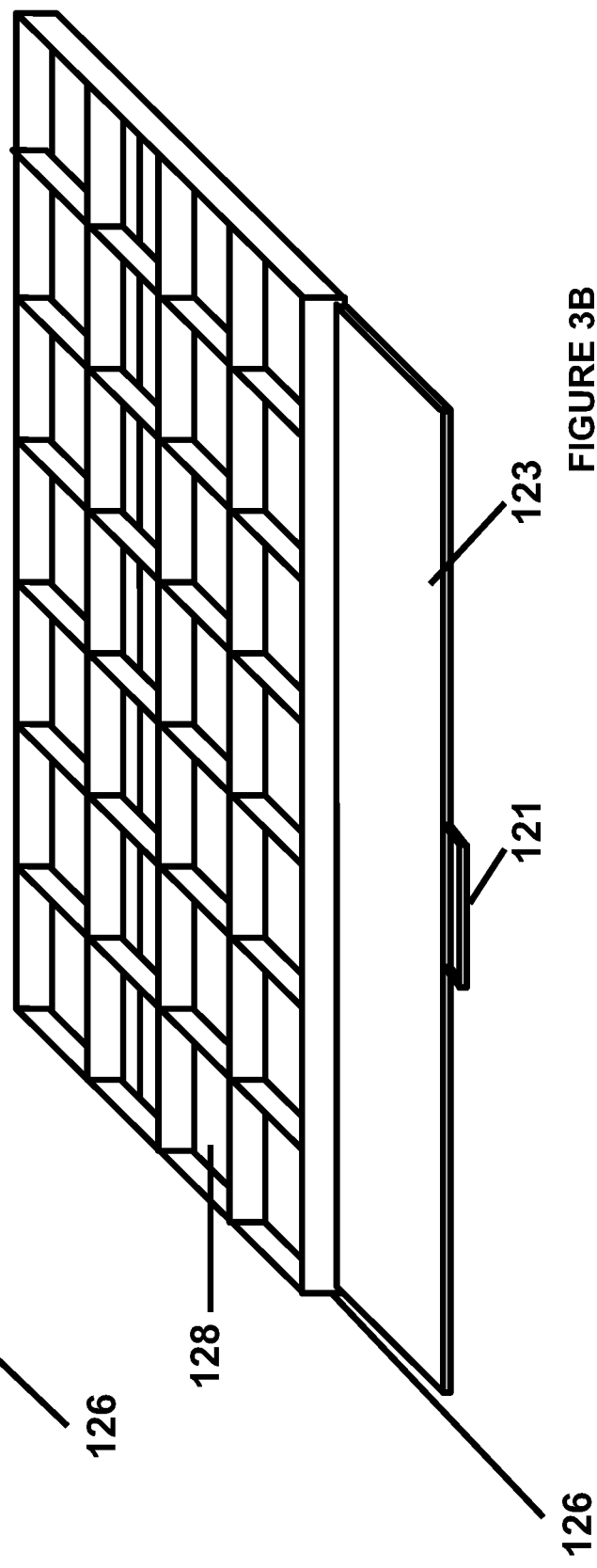

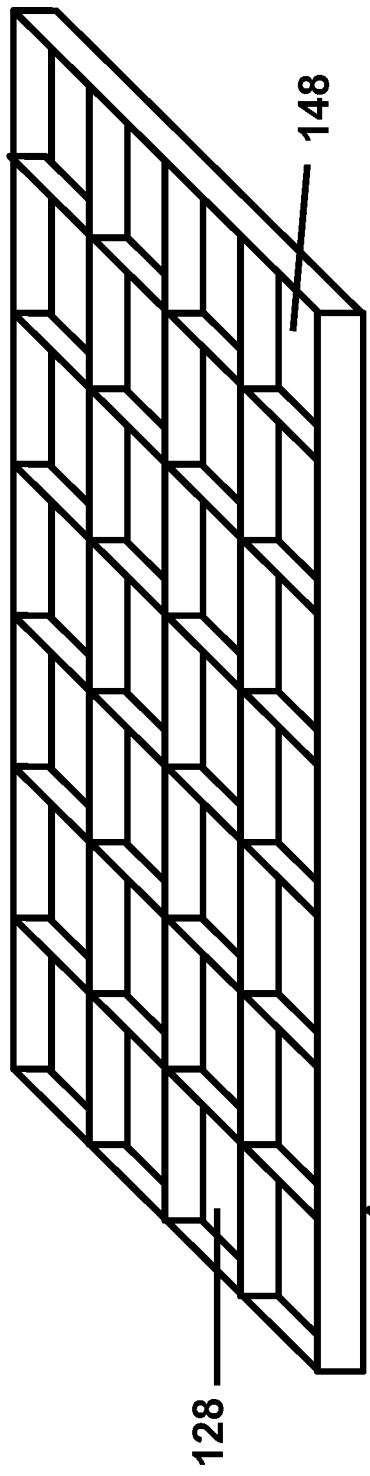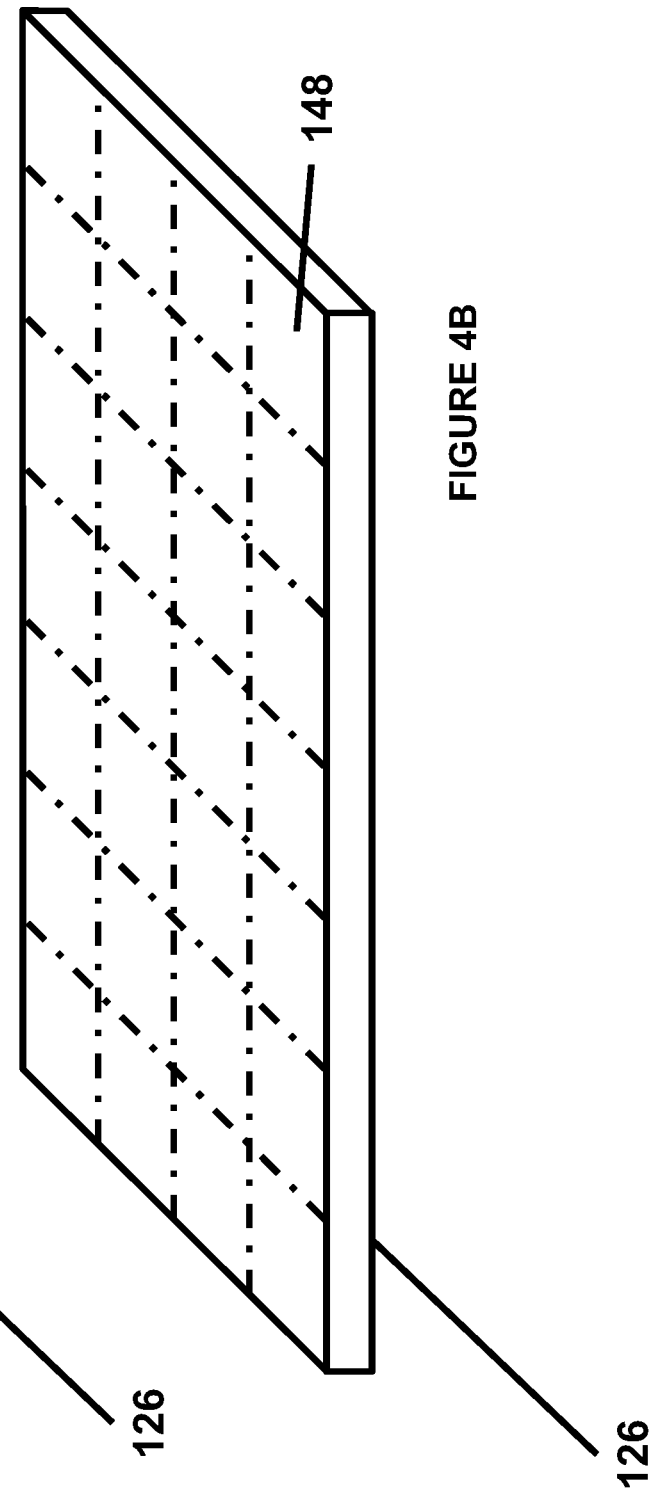

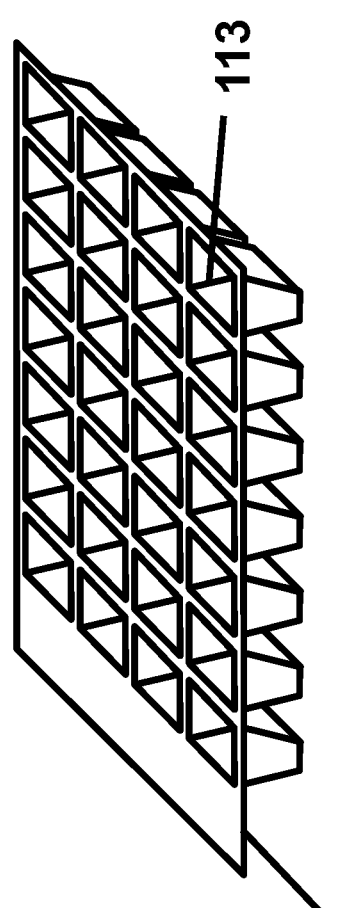
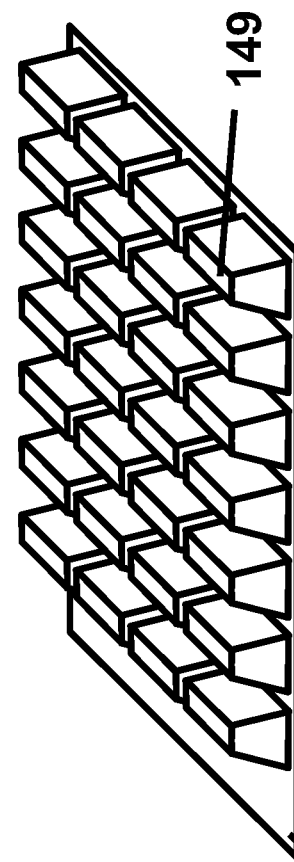

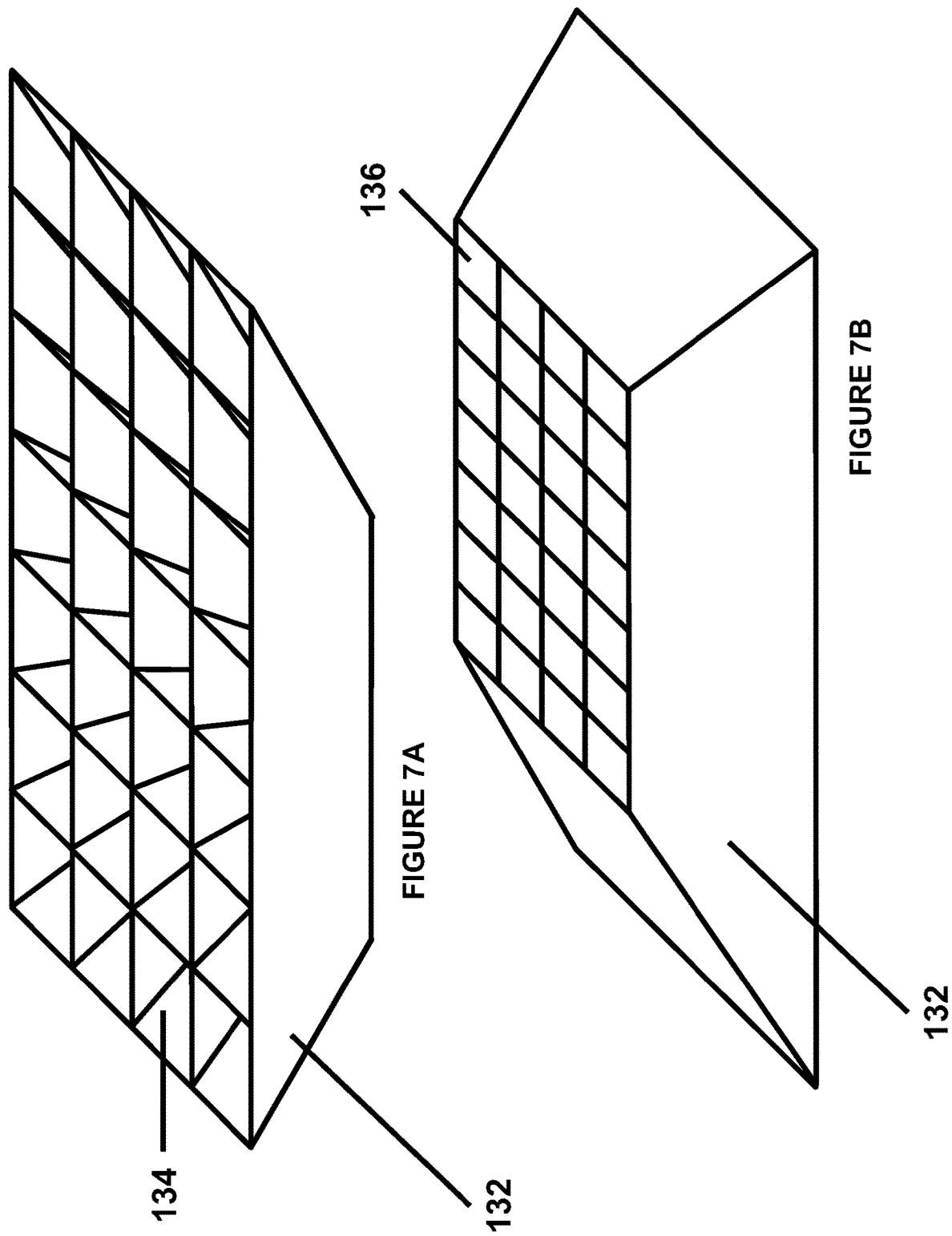

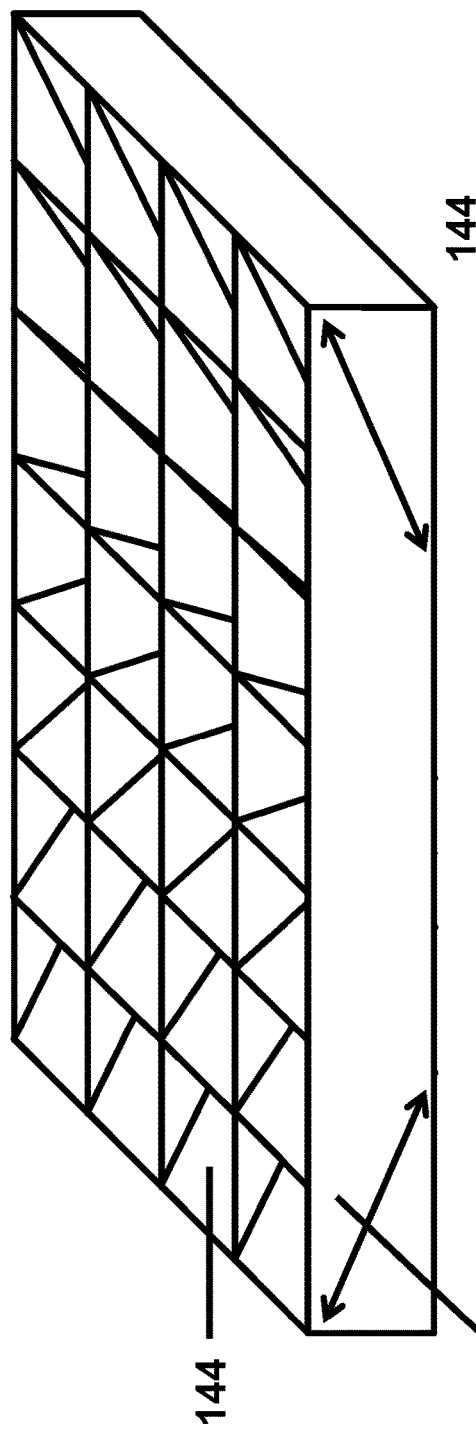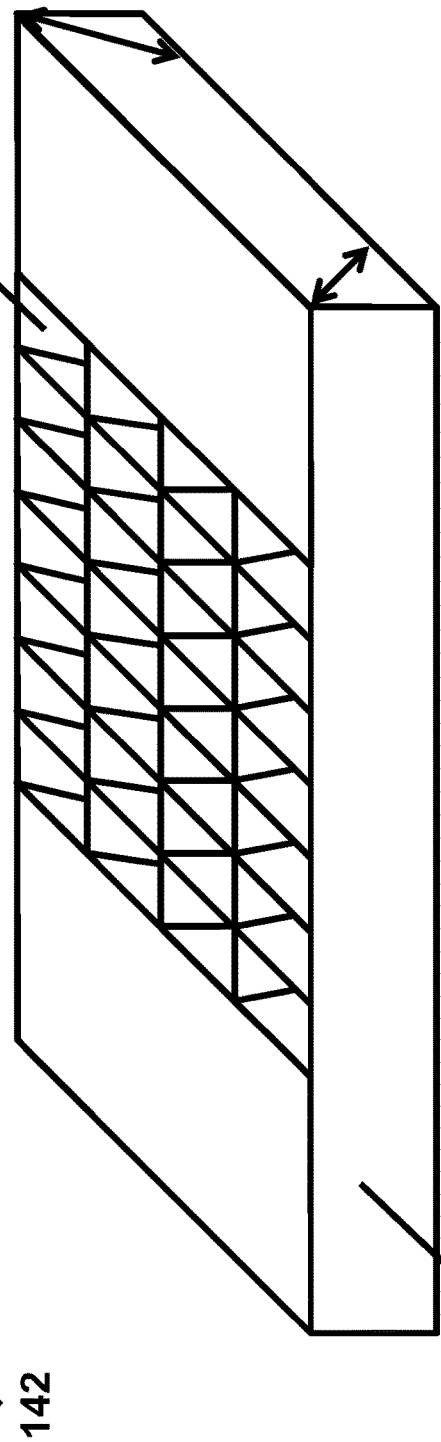
FIGURE 8A
FIGURE 8B

SYSTEMS AND METHODS FOR IDENTIFYING MEDICINES DEPOSITED IN A COMPARTMENT OF A PILL BOX ACCORDING TO A PRESCRIPTION

CROSS-REFERENCE TO RELATED APPLICATIONS

The present application is a 35 USC 371 national stage entry of PCT/CA2017/050763 filed on Jun. 22, 2017 and which claims priority on Canadian patent application No. 2,933,860 filed on Jun. 23, 2016. These documents are hereby incorporated by reference in their entirety.

FIELD OF THE INVENTION

This invention relates to methods and equipment for reducing medical errors, and more specifically when identifying medicines by their external characteristics.

This invention relates to systems and equipment permitting the identification and verification of medicines (tablet/gelcap/capsule and other dry forms) previously deposited in the cells/compartments of a medicine dispenser (blister card/pillbox/weekly organizer/dosette/pill dispenser).

This invention also concerns the methods for producing these systems as well as the methods for using these systems and this equipment.

PRIOR ART

In pharmacies, pharmacists dispense the medications specified by physicians' prescriptions to patients. The administration of prescriptions is generally organized according to four times of day: morning (breakfast), noon (lunch), evening (dinner) and bedtime.

The medications are supplied by wholesalers and pharmaceutical companies in large size packaging. The pharmacy technical assistants prepare the quantities of each medication according to the administration plan validated by the pharmacist and according to the doctor's prescription. For each week, the medications are placed in the cells of the blister card, several medicines can be combined in the same cell corresponding to a given administration time. Preparation of the medications in their final packaging is a step that necessitates large quantities of manpower, which can be a source of error and can result in dosage errors and/or errors in the type of medication ultimately present in the blister card.

Once the blister card has been prepared by the pharmacy technical assistant according to the administration plan validated by the pharmacist, the blister card is sent to the pharmacist for verification. The pharmacist then checks the content of each cell by comparing it to the administration plan. To determine the match between the medication present and what is needed, he relies on his memory, and if that is not possible, he compares the medication present in the blister card to a photo that he displays on a computer screen. This phase requires a lot of time and attention on the part of the pharmacist and presents risks of error in the event medications with similar physical characteristics are present at the same time. This verification is often done under strong time constraints, because the pharmacist is at the end of the chain and he is the only one authorized to release prescriptions. The pharmacist approves the content of the blister card by affixing an adhesive sheet over it, which prohibits any future modification of the content of the blister card.

The medications packaged in the blister card are dispensed to the patient. The doctor's prescription is archived at the pharmacy. The patient or the caregiver therefore no longer has the option of checking the content of the blister card against the prescription.

According to Stat Ramq [Official Statistics Databank] data, in Quebec more than 16,300,000 medications are dispensed in blister cards every year. According to To Err Is Human Building a Safer Health System NATIONAL ACADEMY PRESS Washington, D.C. 1999, in the United States, estimates show that on average 20 people die each day as a result of dispensing errors in hospitals. 1.5 million people per year are harmed by dispensing errors, and the direct and indirect cost of this type of error is USD 15 to 20 billion per year in Europe and in the USA. Ensuring that each patient receives the right dose at each period can prove to be difficult and lead to errors.

International patent application WO 2015/126254 describes equipment and a method for verifying individual doses of medications before they are placed in a compartment.

The patent application published under the number US 2015/0350570 describes a method for the surface scanning of a medication.

The patent application published under the number US 2013/0142406 describes a method and device for verifying a medication prescription.

The patent application published under the number US 2012/0290129 describes a system and method for inspection prior to placing a medication in a compartment.

The patent application published under the number US 2012/0201434 describes a system and method for inspecting packaged medications through comparison of images.

The patent application published under the number US 2006/0045323 describes a system for counting and inspecting objects that do not overlap.

A need existed for a technological solution lacking at least one of the disadvantages of the prior art equipment and methods.

A need therefore also existed for methods for producing simple, reliable equipment lacking at least one of the disadvantages of the prior art processes.

A need therefore also existed for a technological solution lacking at least one of the following disadvantages:
 lack of reliability or incomplete reliability;
 high operating time resulting in a substantial inspection cost; and inapplicable in case of a power outage.

SUMMARY OF THE INVENTION

One aspect of this invention concerns a medication identification method, and consists of:
identifying, from the top, at least one first medication deposited in a compartment of a pill box and analyzing at least one identifying characteristic of said at least one first medication;
identifying, from the bottom, at least one second medication deposited in this compartment of the said pill box and analyzing at least one identifying characteristic of said at least one second medication;
comparing this at least one characteristic of said at least one first medication and this at least one characteristic of said at least one second medication, to determine at least one validated medication;
comparing this at least one characteristic of said at least one validated medication to medication signature characteristics, obtaining an identified content for this compartment; and
comparing the identified content to a prescription.

Another aspect of this invention concerns a medication identification system and comprises:

a first measuring device for identifying, from the top, at least one first medication deposited in a compartment of a pill box and analyzing at least one identifying characteristic of said at least one first medication;

a second measuring device for identifying, from the bottom, at least one second medication deposited in this compartment of said pill box and analyzing at least one identifying characteristic of said at least one second medication;

a comparison device for comparing said at least one characteristic of said at least one first medication and said at least characteristic of said at least second medication, to determine at least one validated medication and comparing said at least one characteristic of said at least validated medication to medication signature characteristics;

a validation device for obtaining an identified content for this compartment and comparing the identified content to a prescription.

Another aspect of this invention concerns a medication identification system and consists in:

depositing at least one medication in a compartment;

identifying this at least one medication deposited in this compartment and analyzing at least one characteristic of said at least one medication;

comparing said at least one characteristic of said at least one medication to medication signature characteristics, to obtain an identified content for the compartment;

comparing the identified content to a prescription; and allowing the medication to pass, via gravity, from the compartment to a pill box.

Another aspect of this invention concerns a medication identification system and comprises:

a compartment sized to receive at least one medication; an identification device making it possible to identify this at least one medication and to analyze at least one identifying characteristic of said at least one medication; a comparison device allowing for comparing said at least one characteristic of said at least one medication to medication signature characteristics to obtain an identified content for the compartment;

a validation device making it possible to compare the identified content to a prescription; and a connection device to allow this at least one medication to pass, via gravity, from the compartment to a cell of a pill box.

Another aspect of this invention relates to a multi-stage system for identification and validation of medications deposited, according to a prescription, in the compartments of a dispenser intended for a patient and/or intended for a patient caregiver, comprising: a first dispenser intended for the patient and/or a patient caregiver; a second dispenser oversized compared to the size of the first dispenser, comprising the same number of compartments or a higher number of compartments than the first dispenser;

a connection device between the compartments of the first dispenser and those of the second dispenser, this connection device allowing the passage of one or more medications from a compartment of the second dispenser to the opposite compartment of the first dispenser, the lower part of a compartment of the second oversized dispenser being configured to have a release device allowing, on demand, the medications of one of the compartments of the second dispenser to migrate to the opposite compartment of the first dispenser;

a measuring device configured to analyze the identifying characteristics of the medications arranged so that they do not overlap in each of the compartments of the oversized dispenser: whether one of the medications present in a compartment is separated by a space from one or more neighboring medications or is in contact with one or more adjacent medications; a transmission device configured to transfer the identifying characteristics (analyzed or not analyzed) gathered by the measuring device and relating to the medications present in the compartments of the second dispenser, to a calculation unit; and a calculation unit configured to:

isolate the identifying characteristics received from the transmission device for each of the medications effectively present in a compartment of the second dispenser, and identify each of these medications, compare the identifying characteristics isolated in the preceding step with the information contained in a database of characteristics of medications that, according to the prescription, should be present in one of the compartments of the dispenser, and this identification and validation system sending a message according to which:—all the medications effectively present in each of the compartments of the second dispenser correspond or not to those that, according to the prescription, should be present there; and/or—the number of medications effectively present in a compartment corresponds to the number of medications that should, according to the prescription, be present there; and/or the total number of medications present in all the compartments of the dispenser corresponds to the total number of medications that should, according to the prescription, be in the dispenser; and/or the weight of the medications present in a compartment corresponds to the weight of the medications that should, according to the prescription, be present there and/or the weight of all the medications present in all the compartments of the dispenser corresponds to the total weight of all the medications that, according to the prescription, should be present there.

Another aspect of this invention concerns equipment for assessing the conformity of the content of a blister card medication dispenser, comprising n compartments, n being an integer higher than or equal to 7, to a prescription, comprising:

a first and a second medication dispenser, the second dispenser being oversized compared to the first dispenser;

a connection device between the compartments of the first dispenser and those of the second dispenser, said device allowing the movement, preferably via gravity, of one or more medications from a compartment of the oversized second dispenser to its opposite compartment in the first dispenser, this connection device preferably consisting of a bundle of conduits with each of the conduits of the bundle being:

in its upper part united with the lower part of one of the compartments of the second oversized dispenser, and in its lower part united with the upper part of a compartment of the first dispenser opposite it, in which equipment:

the lower part of a compartment of the oversized dispenser being configured to have a release device allowing, on demand, the medications of at least one of the compartments of the second dispenser to migrate to the opposite compartment of the first dispenser, and the upper opening of a connection conduit preferably being larger than the lower orifice of the connection conduit.

Another aspect of this invention concerns a system for identifying and validating medications deposited, according to a prescription, in the compartments of a blister pack dispenser intended for a patient and/or a patient caregiver comprising n compartments with n being an integer higher than or equal to 7 and comprising parallel and adjacent rows of compartments, each of the medications being able to be at least partially superimposed with at least one other medication present in the same compartment of the dispenser, comprising:

a measuring device configured to gather identifying characteristics of the medications deposited in each of the compartments of the dispenser;

a transmission device configured to transfer, to a calculation unit, the identifying characteristics gathered by the measuring device; and a calculation unit configured to determine, from the identifying characteristics gathered, if each of the medications effectively present in each of the compartments corresponds or not to a medication that, according to the prescription, should be present there and/or to indicate which compartment contains the non-correspondence(s) and/or what the nature of the non-correspondence(s) is.

this system also being characterized in that:

the measuring device comprises more than one chemical and/or physical analysis device positioned in staggered planes; and/or this measuring device comprising a single chemical and/or physical analysis device that can be moved to different positions in space; and the dispenser has an at least partially flexible or pliable structure making it possible to distort the dispenser at least partially, and as necessary, to allow the measuring device to have better access to one or more of the compartments to be observed.

BRIEF DESCRIPTION OF THE FIGURES

The examples presented in this section of the figures are non-limiting and are presented to exemplify different variants of the technology of this disclosure by illustrating these variants.

FIG. 3A is a perspective view of a preparation tray.

FIG. 3B is a perspective view of a preparation tray with the drawer in a refracted position.

FIG. 4A is a perspective view of a preparation tray.

FIG. 4B is a perspective view of the preparation tray in inverted position.

FIG. 5A is a perspective view of the pill box.

FIG. 5B is a perspective view of the pill box in inverted position.

FIG. 7A is a perspective view of a connection device.

FIG. 7B is a perspective view of the connection device positioned upside down.

FIG. 8A is a perspective view of a connection device.

RECTIFIED SHEET (RULE 91.1)

FIG. 8B is a perspective view of the connection device in an upside down position.

Figure 9:
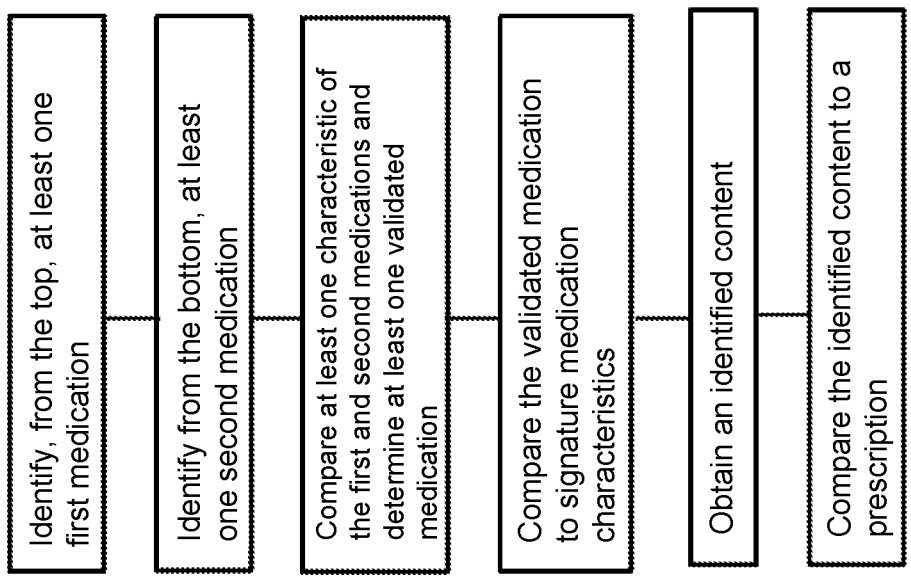

FIG. 9 describes a method for identifying medications according to one aspect of the invention.

DETAILED DESCRIPTION OF THIS INVENTION

The examples presented in this section are non-limiting and are presented to exemplify different variants of the technology of this invention.

Preliminary Definitions

Medication: in its broad sense applicable to the general nature of this disclosure, it concerns any item that is to be placed in a dispenser equipped with compartments and according to dispensing instructions in the compartments of said dispenser.

Prescription: means any instruction for dispensing items in the compartments of a dispenser.

The identification system comprises a device that is configured to analyze the identifying characteristics of the medications placed in the blister card: shape, geometric characteristics, size, color, dimensions, texture, markings. The characteristics of each of the medications of the blister card are isolated, then compared with the information contained in the database, which permits their identification. The details of the identified content of the blister card are compared with the prescription information. The blister card is also called a pill box or a blister pack.

According to one configuration of the medication identification method, the pill box is flexible.

According to another configuration of the medication identification method, the compartment is transparent.

According to one configuration, the medication identification method consists in: identifying, from the top, at least one first medication deposited in a compartment of a pill box and analyzing at least two identifying characteristics of said at least one first medication; identifying, from the bottom, at least one second medication deposited in this compartment of said pill box and analyzing at least two identifying characteristics of said at least one second medication.

For example, the identifying characteristics are chosen from among a shape, a size, a color, a dimension, a texture and a marking.

For example, the first medication is identified by means of a camera.

For example, the second medication is identified by means of a camera.

For example, the first medication and the second medication may be identical.

For example, the first medication and the second medication are different.

According to a configuration of the medication identification system, the first measuring device comprises a camera to capture a first image of the compartment.

For example, the second measuring device comprises a camera for capturing a second image of the compartment.

The identification system may include:
a first measuring device for identifying, from the top, at least one first medication deposited in a compartment of a pill box and analyzing at least two identifying characteristics of the first medication; and
a second measuring device for identifying, from the bottom, at least one second medication deposited in this compartment of said pill box and analyzing at least two identifying characteristics of the second medication.

The identifying characteristics are chosen from among a shape, a size, a color, a dimension, a texture and a marking.

For example, the pill box is flexible. The compartment may be transparent.

The first medication deposited may be identified by means of a camera. The second medication deposited may be identified by means of a camera.

For example, the first medication and the second medication may be identical. According to another configuration, the first medication and the second medication may be different.

An enclosure may receive the medication identification system. The enclosure may be flexible.

For example, the medication identification method includes the activation of a retractable drawer allowing the medication to pass, via gravity, from the compartment to the pill box. The method may include a step for associating the prescription with the compartment of the tray.

The method may include a step for measuring and checking a compartment weight.

For example, the medication identification method consists in identifying a medication deposited in the compartment and analyzing at least two characteristics of the medication. The characteristics of the medication may be chosen from among a shape, a size, a color, a dimension, a texture and a marking.

For example, the medication identification system has a connection device that comprises a retractable drawer. The connection device may include a trapezoidal prism fitted with various channels making it possible to connect the compartments with the cells. The connection device may include an upper base and a lower base, the bases being connected by means of multiple channels allowing passage from the compartments to the cells. The lower surface of the compartment may be larger than the lower surface of the cell of the pill box. The internal volume defined by the compartment may be greater than the internal volume defined by the cell of the pill box.

For example, the medication identification system has an identification device allowing the identification of at least one medication and analysis of at least two identifying characteristics of at least one medication. The characteristics of the medication are chosen from among a shape, a size, a color, a dimension, a texture and a marking. A kit may include the medication identification system and a pill box.

A first aspect of this invention comprises identification and validation systems for medications deposited, according to a prescription, in the compartments of a dispenser comprising n compartments, n being an integer greater than or equal to 1, each of medications being able to be at least partially superimposed with at least one other medication present in the same compartment of the dispenser, said system comprising:
a measuring device configured to gather the identifying characteristics of the medications deposited in each of the compartments of the dispenser;
a transmission device configured to transfer, to a calculation unit, the identifying characteristics gathered by the measuring device;
a calculation unit configured to determine, from the identifying characteristics gathered if
each of the medications effectively present in each of the compartments corresponds or not to a medication that, according to the prescription, should be present there and/or to indicate which compartment contains the non-correspondence(s) and/or what the nature of the non-correspondence(s) is.

The methods for producing the systems of this disclosure, particularly those using at least one of the known assembly techniques such as: screwing, gluing, bolting, dovetailing, riveting and welding, are also part of the subject matter of this disclosure.

The uses of the medication identification and validation system, as defined previously or as obtained by the production processes defined previously, to reduce the risk of error when filling a medication dispenser according to a prescription, are also part of the first aspect of this disclosure.

The methods for validating the conformity, to a prescription, of the filling of a medication dispenser, and consisting of the following steps:
filling, according to a prescription, of the compartments of a dispenser, by an operator and/or by an automaton;
determination, thanks to the use of at least one of the identification systems according to this invention, of the content of each of the compartments; and
potential correction of the content of one or more compartment(s) of the dispenser in case of non-conformity established by this system compared to the medical prescription, are also part of the first aspect of this disclosure.

A second aspect of this invention consists of multi-stage identification and validation systems for medications deposited, according to a prescription, in the compartments of a dispenser intended for a patient and/or intended for a patient caregiver, these medications being able to be at least partially superimposed with at least one other medication present in the same compartment of the dispenser, this system comprising:
a first dispenser intended for the patient or for a patient caregiver;
a second oversized dispenser (compared to the size of the first dispenser) comprising the same number of compartments or a number of compartments greater than the number of compartments of the first dispenser, this second dispenser preferably being large enough to prevent the covering of medications, and preferably positioned higher than the first dispenser, and advantageously above or offset;
a connection device between the compartments of the first dispenser and those of the second dispenser, said connection device allowing the movement, preferably via gravity, of one or more medications from a compartment of the second dispenser to its opposite compartment in the first dispenser, said connection device preferably consisting of a bundle of conduits, preferably more or less parallel, each of the conduits being:

in its upper part united with the lower part of one of the compartments of the second dispenser, and
i.—in its lower part united with the upper part of the compartment of the first dispenser opposite it;
the lower part of a compartment of the oversized second dispenser being configured to have a release device allowing, on demand, the medications of at least one of the compartments of the second dispenser to migrate to the opposite compartment of the first dispenser, and
the upper opening of a conduit of the connection device preferably being larger than the lower orifice of the connection conduit;
a measuring device configured to analyze the identifying characteristics of the medications arranged so as not to overlap one another in each of the compartments of the oversized dispenser: whether one of the medications present in a compartment is separated by a space from one or more neighboring medications or they are in contact with one or more adjacent medication(s);
a transmission device configured to transfer the identifying characteristics (analyzed or not analyzed) gathered by the measuring device and relating to the medications present in the compartments of the second dispenser, to a calculation unit;
a calculation unit configured to:
isolate the identifying characteristics received from the transmission device for each of the medications effectively present in a compartment of the second dispenser, and identify each of these medications,
compare the characteristics isolated in the preceding step with the information contained in a database of characteristics of medications that, according to the prescription, should be present in one of the compartments of the dispenser, and said identification and validation system sending a message according to which:
i) all the medications effectively present in each of the compartments of the second dispenser correspond or not to those that according to the prescription should be present there the number of medications effectively present in a compartment corresponds to the number of medications that should, according to the prescription, be present there; and/or
the total number of medications present in all the compartments of the dispenser corresponds to the total number of medications that should, according to the prescription, be in the dispenser; and/or
the weight of all the medications present in a compartment corresponds to the weight of the medications that should, according to the prescription, be present there and/or the weight of all the medications present in all the compartments of the dispenser corresponds to the total weight of all the medications that, according to the prescription, should be present there.

The methods for producing the multi-stage identification systems, through the use of at least one of the known assembly techniques such as: screwing, gluing, bolting, dovetailing, riveting and welding, are also part of this disclosure.

The uses of the multi-stage identification systems, to reduce the risk of error when filling a medication dispenser according to a prescription are also part of this disclosure.

The methods for validating the conformity to a prescription, of the filling of a medication dispenser comprising the following steps:
filling of the compartments of an oversized dispenser according to a medical prescription;
determination of the content of each of the compartments thanks to the use of an identification system; and
potential correction of the content of one of the compartments of the dispenser in case of established non-conformity compared to the medical prescription; and
transfer of the medications present in a compartment of the oversized dispenser into the opposite compartment of the first dispenser, are also part of this disclosure.

Another aspect of this disclosure includes equipment for assessing the conformity of the content of a medication dispenser to a prescription, comprising:
a first and a second medication dispenser, the second dispenser being oversized compared to the first dispenser;
a connection device between the compartments of the first dispenser and those of the second dispenser, said device allowing the transfer, preferably via gravity, of one or more medications from a compartment of the second dispenser to its opposite compartment in the first dispenser, this connection device preferably consisting of a bundle of conduits with each of the conduits of the bundle being:
in its upper part united with the lower part of one of the compartments of the second dispenser, and
i.—in its lower part united with the upper part of a compartment of the first dispenser opposite it;
the lower part of a compartment of the oversized dispenser being configured to have a release device allowing, on demand, the medications of one of the compartments of the second dispenser to migrate to the opposite compartment of the first dispenser, and
the upper opening of a connection conduit preferably being larger than the lower orifice of the connection conduit.

The methods for producing the assessment equipment through the use of at least one of the known assembly techniques such as: screwing, gluing, bolting, dovetailing, riveting and welding, are also part of this disclosure.

The uses of the equipment to reduce the risk of error when filling a medication dispenser according to a prescription are also part of this disclosure.

The methods for validating the conformity to a prescription, of the filling of a medication dispenser integrated in conformity assessment equipment, said method including the following steps:
filling of the compartments of an oversized dispenser according to a medical prescription;
determination of the content of each of the compartments of the oversized dispenser;
potential correction of the content of one of the compartments of the oversized dispenser in case of established non-conformity compared to the medical prescription; and
transfer of the medications present in a compartment of the oversized dispenser into the opposite compartment of the first dispenser, are also part of this disclosure.

The prototype of this disclosure allows verification of the content of the blister card containing one or more medications. The verification can be done automatically. The verification can be done without any human contact. The verification of the characteristics of the medications contained in the blister card is carried out according to an identification of each of the characteristics of the medications using two dimensional and three dimensional data as data of a "point cloud," obtained by different systems and/or methods.

According to a described prototype, the system may include an imaging device configured to gather surface image data of the content of the cells of the blister card containing one or more medications and a controller configured to control the imaging device for the collection of image data of one or more medications deposited in the cells of the blister card.

The system is configured to:
produce a 3D point cloud from the surface image data of one or more medications contained in the cells of the blister card;
produce geometric data for each of the medications from the 3D point clouds;
produce two dimensional image data for each of the medications.
produce data for each of the medications including the characteristics of their external appearance other than geometric characteristics such as their color, for example;
precisely identify the medication corresponding to each of the medications contained in the cells of the blister card based on the characteristics (geometric and other) produced by the two dimensional and three dimensional data (3D point cloud).

According to a described prototype, a program may provide the instructions to the computer for carrying out the steps for identifying the medications based on their characteristics (geometric and/or other) obtained from an imaging device. The method includes receipt of the characteristics (geometric and/or other) of a medication, as well as the characteristics produced from the two dimensional and three dimensional data (3D point cloud) of a medication. The method also includes the determination that the characteristics (geometric and/or other) of the medication(s) present in the cells of the blister card correspond to the characteristics (geometric and/or other) of a known medication.

This disclosure is not limited to an identification of the medications through optical recognition alone, but may include another method or apparatus to complete this recognition such as a laser or spectrometer.

The medications inspected include but are not limited to the following compounds:
pharmaceutical products;
nutraceuticals;
vitamins;
food supplements;
gelcaps;
capsules; and
medications, with or without prescription.
And any other medication that can be packaged in a wrapping, packaging or a container.

Analysis and inspection methods for the medications contained in the cells of an individual container set for medications The identifying information obtained for the medications contained in the cells is compared to the information saved previously in the database for each of the medications indicated by the prescription. A comparison with the characteristics of similar medications is also performed.

The characteristics of the medications (size, shape, volume, color, density, texture, exterior surface, marking, luminescence, etc.) present in the individual containers are obtained by analytical methods and equipment including, but not limited to:
2D visible light sensor (photo or video);
3D visible light sensor (photo or video);
X-ray;
RGB decomposition, color analysis under different colored lighting including white light, ultraviolet light, red light, green light, blue light and/or infrared light, stroboscopic light;
optical character recognition (OCR) and/or optical character verification (OCV);
spectroscopic analysis (near infrared, fluorescence);
MMS (multimodal multiplex sampling) and Raman spectroscopy;
magnetic resonance imaging;
ultrasound;
laser excitation scanner;
precision weighing; and any other chemical and/or physical analysis method.

The following examples are given by way of illustration only and are not to be interpreted as constituting any limitation of the general nature of this disclosure.

Example 1

Method with Closed Housing

System Details
In a configuration, the system of this disclosure includes:
a housing containing
a holder on which is positioned a medication dispenser containing the medications to be inspected,
the size of the holder is approximately 21×21 cm;
lighting devices positioned in the corners of the housing.
imaging devices allowing the acquisition of the data analyzed by the calculation unit;
an optical scanning verification system to verify the content of the preparation tray, the optical system may be stationary or mobile and move along two horizontal axes in order to inspect the entire surface of the cells of the tray; and a precision scale may be added to check the weight of all of the medications.

Steps for Implementing the Method of Use
1. A filled blister card medication dispenser is placed in the holder;
2. The medications placed on the tray are counted and verified by an optical scanning system. For example, an optical scanning system as described in the EyeCon® system marketed by the company Avery Weigh-Tronix may be used;
3. Validation of the content by the verification system compared to the prescription;
4. Removal of the blister card medication dispenser by the operator; and
5. The blister card is sealed with a sealing sheet by the operator.

According to one aspect of this application, a method for identifying medications is disclosed. In reference to FIG. 9, a medication identification method is described. The method consists in identifying, from the top, at least one first medication deposited in a cell of a pill box and analyzing at least one identifying characteristic of the first medication. The first medication can be identified from an image taken from the top of the pill box. The method also consists in identifying, from the bottom, at least one second medication deposited in the cell of the pill box and analyzing at least one identifying characteristic of the second medication. The second medication can be identified from an image taken from the bottom of the pill box.

The method consists in comparing at least one characteristic of the first medication and at least one characteristic of the second medication, to determine at least one validated medication. The method also consists in comparing at least one characteristic of the validated medication to medication signature characteristics, to obtain an identified content for the cell; The method also consists in comparing the identified content to a prescription.

According to one aspect of this application, a medication identification system is disclosed. An example of the medication identification system 100 is presented in FIG. 1. The identification system 100 includes an enclosure 101. The enclosure may be a housing or a box. The shape of the enclosure may be a prism with a rectangular or square base. The base of the enclosure may have any other shape, for example a shape with 3, 4, 5, 6, 7 sides, etc.

The enclosure 101 may be flexible and may be easily distorted. For example, the enclosure 101 may be made with a flexible material. For example, the flexible material may be plastic, cardboard, metal, etc. The enclosure 101 may have a door 107. The door 107 makes is possible to open and close the enclosure 101. By opening the door 107, a user has access to the enclosure 101. The door 107 may have a manual or automatic closing device. The enclosure 101 has a ceiling 111. The ceiling 111 has an interior surface and an exterior surface.

The enclosure 101 has a floor 113. The floor 113 has an interior surface and an exterior surface. The enclosure has walls. For example, the enclosure 101 has one of walls 106 and 109. Walls 106 and 109 may each have an interior surface and an exterior surface. The interior surface of walls 106 and 109 may have a device for receiving a pill box. For example, the interior surfaces of walls 106 and 109 may have rails for receiving a pill box.

The identification system 100 may include a pill box 103. The pill box 103 may be integrated in the enclosure. The pill box 103 may also be a separate part of the enclosure. The pill box 103 has cells 102. For example, a cell 102 may be integrated in the pill box. The cell receives at least one medication that is deposited in the pill box. In reference to FIG. 2, the cell 102 has an opening to receive one or more medications. The cell 102 also has a bottom that allows the medications to accumulate inside the cell 102. The cell 102 also has walls. The walls define the interior volume of the cell 102. The pill box may be transparent. The cells of the pill boxes may be transparent.

The medication identification system includes one or more measuring devices. A measuring device is used to identify one or more medications deposited in a pill box. For example, a measuring device may capture an image of a medication deposited in the pill box and, then, analyze the identifying characteristics of the medication to determine what medication is involved.

Figure 2:
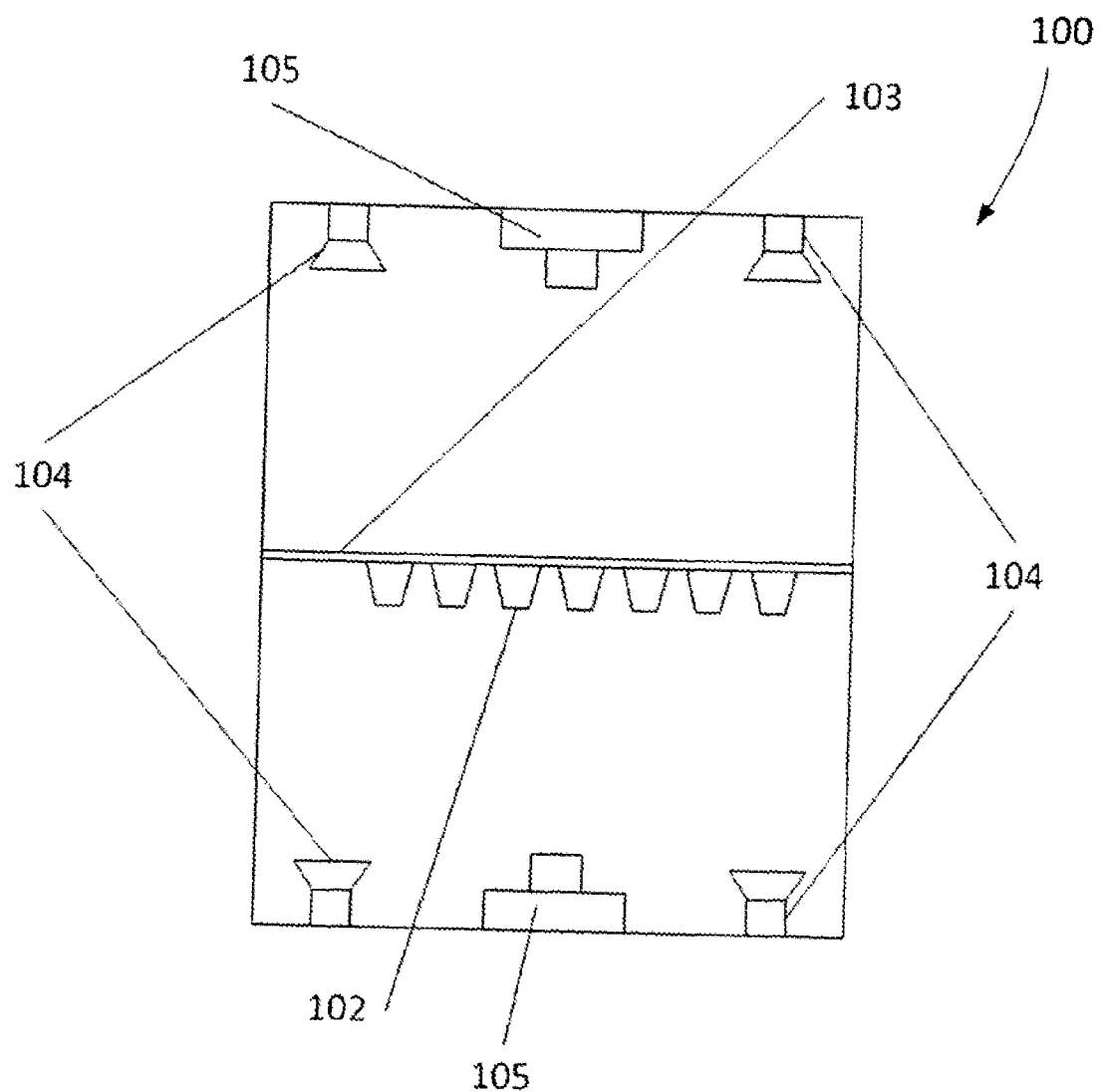
FIG. 2 is a side view and horizontal section of a device for identifying the medications present in the compartments of a medication dispenser, based on their characteristics (geometric and/or other) obtained from an imaging device.

In reference to FIG. 2, measuring devices are inserted in the enclosure 101. A measuring device is inserted in the interior surface of the ceiling 111. A measuring device is also inserted in the surface of the floor 113.

A measuring device may include a lighting system and an imaging system. The lighting system may include a lamp for projecting light inside the enclosure and on the pill box. In reference to FIG. 2, lighting systems 104 are located on the ceiling 111 and on the floor 113. The imaging system may include cameras for taking photos or videos of a pill box. In reference to FIG. 2, imaging systems are located in the ceiling 111 and in the floor 113.

In FIG. 2, the pill box 103 is located inside the enclosure 101. The lighting systems light the interior of the enclosure and the pill box from the ceiling and from the floor. For example, lighting systems may project light directly on the pill box. The imaging devices 105 capture images of the pill box from the top, i.e., from the ceiling. The imaging devices capture images of the pill box from the bottom, i.e., from the floor.

According to one configuration mode, the pill box is transparent. The cells of the pill box are also transparent. As a result, medications that are deposited in the cells of the pill box can be seen from any reference point inside the enclosure. For example, the medications can be seen from the ceiling. The imaging device can capture an image of the pill box including all the medications from the ceiling. The medications can also be seen from the floor of the enclosure because the pill box and the cells are transparent. The visibility of the medications is improved by the lighting system. The imaging device can capture an image of the pill box including all the medications from the floor of the enclosure.

The image of the pill box containing the medications is then analyzed to identify each medication. A medication may be identified from the characteristics specific to this medication. For example, a medication can have a shape, a size, a color, a dimension, a texture or a marking that is specific to it.

For example, each medication has its identifying characteristics that are specific to it and that are different from those of the others. For example, a specific medication may have a series of marked letters and numbers. A specific medication may have an inscription of an alternate color or of a same color as that of the medication itself. The inscription may be engraved on the surface. Each medication may have a particular shape. For example, the shape of the medication may be round, oval, triangular or another shape.

Each medication may have a particular thickness. The measuring device can communicate the image of the pill box to a computer system to identify the medications in the pill box. The computer system isolates each medication in the image. For each medication isolated, the computer system identifies this medication from the characteristics specific to this medication.

For example, in a pill box image taken from the top, the computer system determines that there is a red colored medication with an oval shape and the inscription "FM." From these characteristics, the computer system can determine that the medication is a type Y medication. For example, in an image of the pill box taken from the bottom, the computer system determines that the medication has a capsule shape, with a pink color on one side and a white color on the other side. The computer system also determines that the medication bears the inscription "P 087." From these characteristics, the computer system can determine that the medication is a diphenhydramine.

In one configuration, the medication identification system includes a comparison system for comparing the images of the pill box taken from different angles to better identify the medications. For example, the images of the pill box can be taken from different angles from the top, from the bottom or from the side. For example, a pill box contains medications and an imaging device may be located in the ceiling of the enclosure and take a first image of the pill box from the top. In the same way, another imaging device can be located in the floor of the enclosure and take a second image of the pill box from the bottom. The first and the second image are sent to the comparison system to identify the medications that are in the pill box.

The comparison system may include a comparison device including a computer system. For example, the comparison device may receive two images of the pill box: an image that was taken from the top of the pill box; and an image that was taken from the bottom of the pill box. Because medications can be stacked on top of one another in a cell of the pill box, the comparison of the two images allows a better perspective of the contents of the pill box or of the cells of the pill box. For example, from the compared images, we can determine the number of medications in each cell of the pill box and identify each medication separately.

For example, the computer system may use the image taken from the top of the pill box to identify the characteristics of a medication. From the image taken from the top, the computer system can determine that a medication has a red color and an oval shape. In the same way, the computer system can determine that a medication has an inscription, for example "P087," on its surface. For example, from the image taken from the bottom, the computer system can determine that a medication has a white color and a rectangular shape.

The computer system can use the image taken from the bottom to validate the conclusions compared to the image taken from the top. For example, using the image taken from the bottom of the pill box, the computer system confirms that the medication effectively has a red color and an oval shape.

For example, from the two images, the computer system can determine the number of medications in each cell of the pill box and the characteristics of each medication. For example, from the two images, the computer system can determine that there are two medications in cell A1 of the pill box, the two medications are on top of one another, the one on top is red and has the inscription "P087" on its upper surface and the one underneath is green and has an oval shape.

The computer system compares the characteristics of each medication with the medication signatures in a database that contains characteristic signatures making it possible to identify a medication.

A characteristic signature of a medication is a set of characteristics that are specific to this medication. By determining the characteristics of a medication, the computer system can compare these characteristics to predefined characteristic signatures to identify a medication.

In one configuration, the medication identification system includes a validation system for comparing the identified medication to a prescription. For example, after having identified the content of a pill box cell, the validation system verifies whether these medications correspond to a prescription.

For example, the pill box or a cell of the pill box could correspond to a defined prescription. For example, a prescription contains two type Y medications. The system includes a validation device for obtaining an identified content for the content of the cell and comparing the identified content to a prescription. For example, the validation system can verify that two type Y medications are in the pill box or in one of the cells of the pill box.

For example, a prescription specifies that a type Z medication and a type P medication must be taken two times a day. The computer system may be configured to associate the cells of the pill box to each period when the medications are to be taken. For example, the computer system may associate cells A1 and A2 to two periods of the day when the medications are to be taken. Then, the computer system can determine if the medications in cells A1 and A2 effectively correspond to a type Z medication and a type P medication, as defined in the prescription.

Example 2

Operation Sequences for Recognition of the Medications in the Cells

Method with Closed Housing or Enclosure

The content of the pill box is prepared according to the prescription validated by the pharmacist. The pill box is placed in the holder of the closed housing. Data acquisition is launched by the operator. The acquisition sequence may be alternating or simultaneous for each of the dimensions and/or each of the cells.

Figure 1:
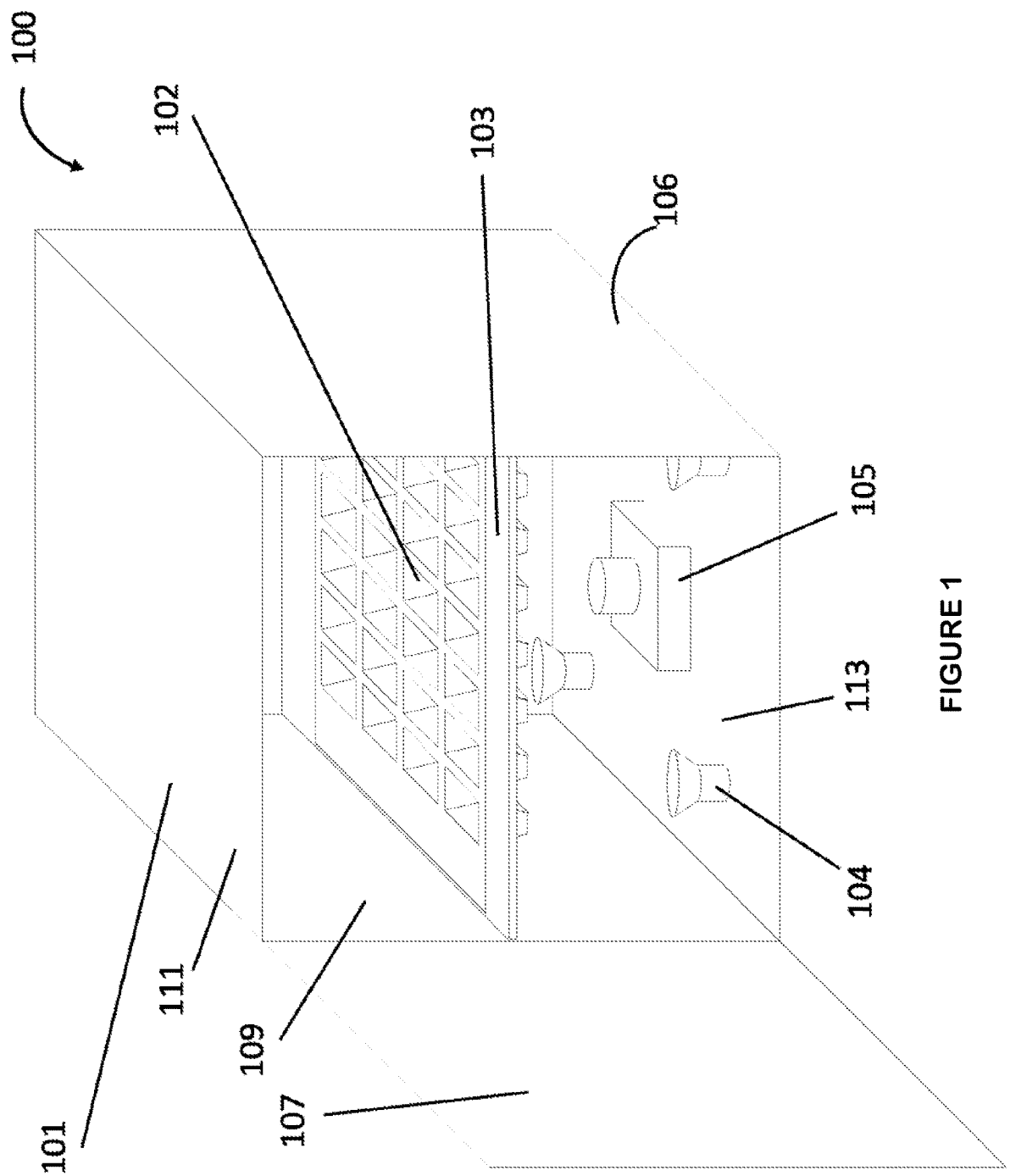
FIG. 1 is a front view in an advantageous embodiment, of the semi-closed structure of a system of this disclosure comprising an imaging device consisting of at least one upper level camera aimed at the upper surface of the compartment and at least one lower level camera aimed at the lower surface of the compartment, a horizontal support and a lighting device comprising 4 lights positioned in the corners of the structure.

The sensor(s) placed at the top transmit(s) the data to the system (see FIGS. 1 and 2). It identifies the characteristic(s) of the medications. The sensor(s) placed at the bottom transmit(s) the data to the system. It identifies the characteristic(s) of the medications.

The system compares and analyzes the pairs of characteristics obtained previously and it assembles all of the characteristics of the medications present in the cell of the pill box.

The system compares the characteristics obtained with the signature characteristics of the databank.

The system identifies the content of the cell.

The system compares the identified content of the cell with the prescription.

The system validates the content of the cell or not.

The sequence is repeated for each of the cells of the blister card alternately or simultaneously.

Example 3

Operation Sequence for Recognition of the Medications in the Cells

Method with Preparation Tray

The content of the large preparation tray is prepared according to the prescription validated by the pharmacist.

The large preparation tray is placed on the preparation tray holder.

Data acquisition is launched by the operator. The acquisition sequence may be alternating or simultaneous for each of the cells.

The sensor(s) placed perpendicular to the large tray transmit(s) the data to the system. It identifies the characteristics of the medications.

The system compares and analyzes the pairs of characteristics obtained previously and it assembles all of the characteristics of the medications present in the cell of the large tray.

The system compares the characteristics obtained with the signature characteristics of the database.

The system identifies the content of the cell.

The system compares the identified content of the cell with the prescription.

The system validates the content of the cell or not.

The sequence is repeated for each of the cells of the blister pack alternately or simultaneously.

Example 4

Method with Tray

System Details

In one configuration, the system of this disclosure includes:
 a verification preparation tray has a number of cells equivalent to the blister pack being prepared, generally 28 cells (7×4 cm). The size of the tray is approximately 32×35 cm (28 cells of 8×5 cm) to allow it to contain all of the medications of a prescription without overlapping;

a retractable drawer under the tray to release the medications from the tray to the pill box.

a set of tubes ensuring the correspondence between the cells of the preparation tray and the cells of the pill box;

an optical scanning verification system for verifying the content of the preparation tray, the optical system may be stationary or mobile and move along two horizontal axes in order to inspect the entire surface of the cells of the tray; and a precision scale may be added to check the weight of all of the medications placed on the tray; and a pill box holder to ensure the exact correspondence of the descending tubes of the inspection tray to the blister card.

In one configuration, the medication identification system includes a compartment capable of receiving at least one medication. The compartment may be a preparation tray or a compartment of a preparation tray. In reference to FIG. 3A, a preparation tray 126 is disclosed. The preparation tray includes a retractable drawer. In reference to FIG. 3B, the drawer 123 is retracted. A handle 121 makes it possible to pull the drawer 123 to retract it.

FIG. 4A shows an example of a preparation tray including compartments 128. FIG. 4B shows an example of a preparation tray in inverted position. FIG. 5A shows an example of a pill box 110 including cells 113. FIG. 5B shows an example of a pill box 110 in inverted position.

Figure 6A:
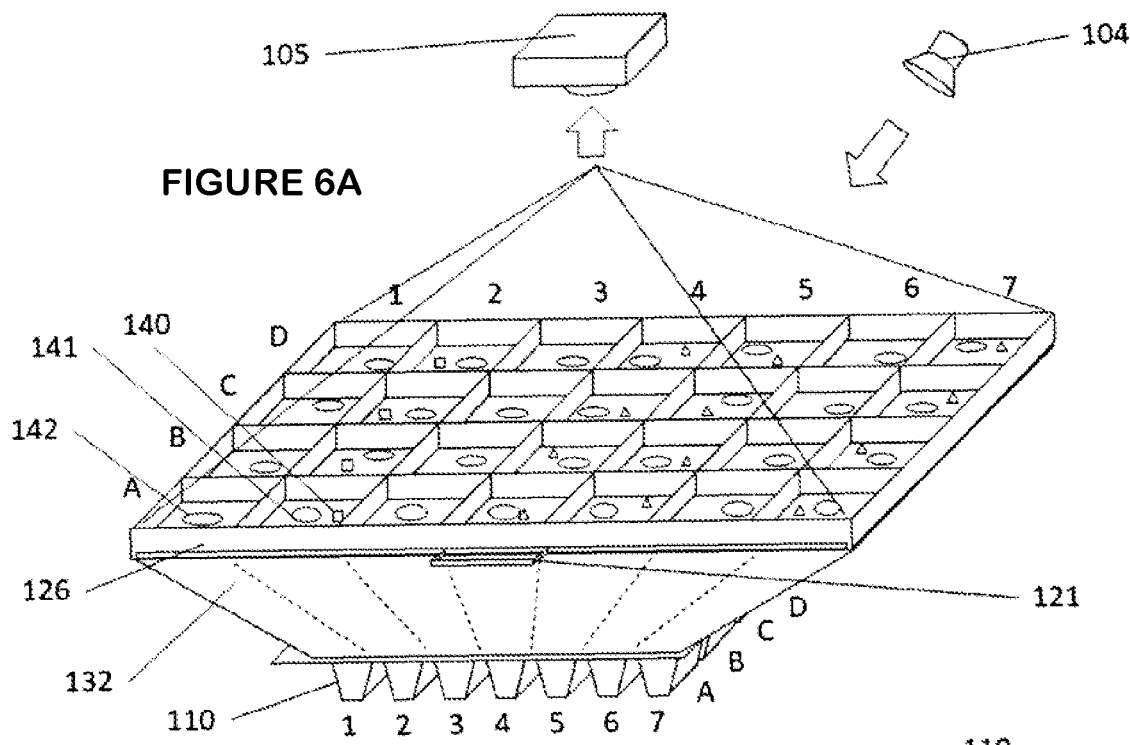
FIG. 6A is a top perspective view of a multi-stage system of this invention, the oversized dispenser being filled with medication according to a prescription and positioned above a standard dispenser; the transfer of the medications from the oversized dispenser to the standard dispenser taking place by means of a bundle of roughly parallel connection conduits placed at the local vertical.

In reference to FIG. 6A, a medication identification system is disclosed. Medications 140, 141 and 142 are deposited in the preparation tray 126. A lighting system 104 projects light onto the tray and an imaging system 105 takes photos or videos of the preparation tray 126. From the images captured by the imaging system, an identification device identifies the medications on the preparation tray 126 to analyze their identifying characteristics. For example, the identification device may determine that a medication has a red color and an oval shape and the inscription "P087." A computer system compares these characteristics with medication signatures in a database. This makes it possible to validate the content of the preparation tray and identify the medications on the preparation tray.

A validation device compares the identified medications to a prescription. This ensures that each compartment of the preparation tray contains the medications of the prescription that correspond to it. A prescription may be associated with the preparation tray or with each compartment of the preparation tray. The medication identification system allows for verifying that the medications corresponding to a specific prescription are located in the compartment corresponding to this prescription.

A connection device allows a medication situated in a compartment to pass via gravity, from the compartment to a cell of a pill box. A drawer can be refracted to allow the medications to pass through the connection device.

Figure 6B:
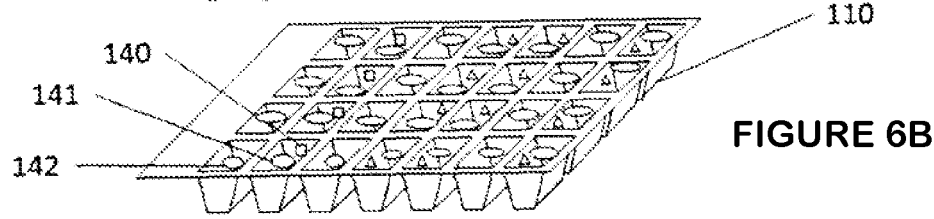
FIG. 6B: is a top perspective view of the standard dispenser after the medications present in the upper dispenser have been transferred to it.
Figure 6C:
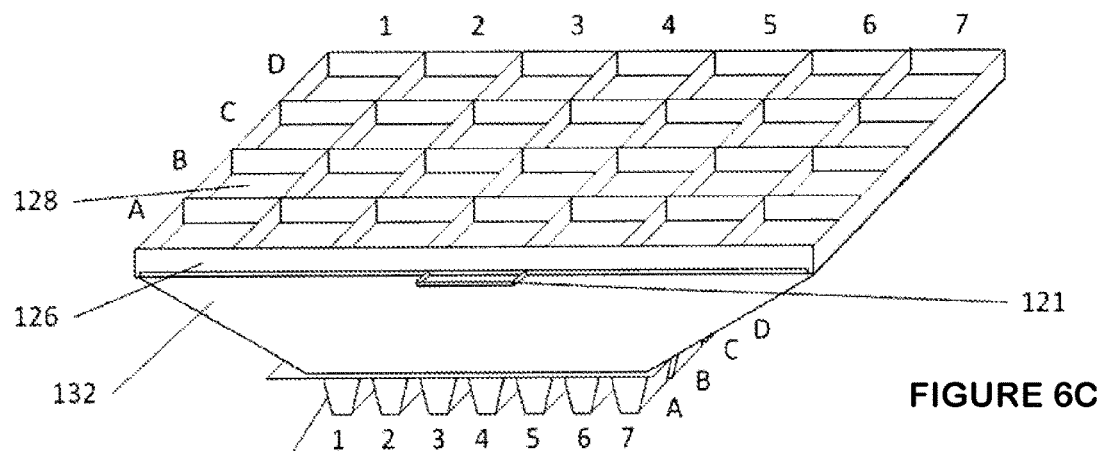
FIG. 6C is a perspective view of the multi-stage system.
Figure 6D:
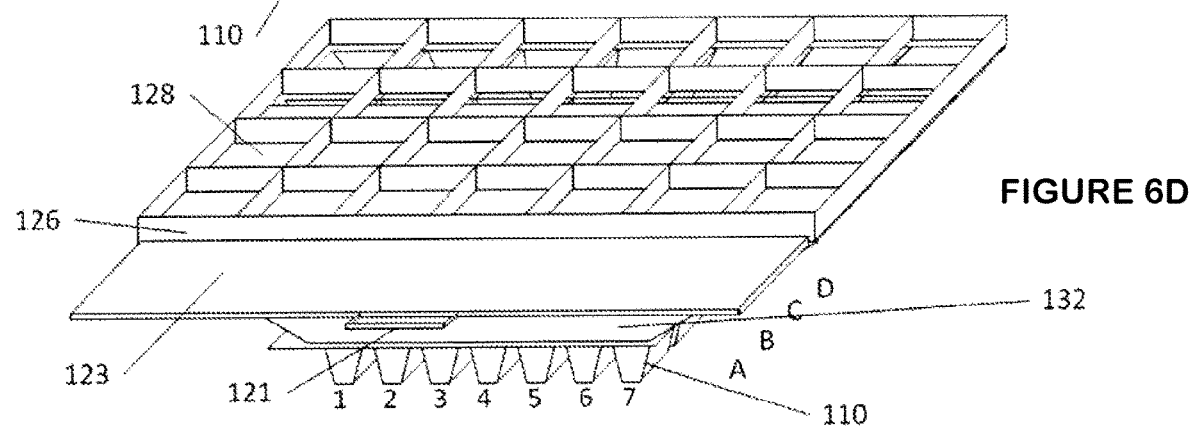
FIG. 6D is a perspective view of the medication identification system with the drawer in a retracted position. inverted.

In reference to FIGS. 6A and 6D, a retractable drawer 123 has a pull/handle 121. By retracting the drawer 123 using the pull/handle 121, the medications pass via gravity from the preparation tray 126 to a pill box 110. A connection device 132 is a conduit with passages allowing the medications located on the preparation tray to pass into the cells of the pill box 110.

For example, in reference to FIG. 6A, medication 142 is located in cell A1 of the preparation tray and medications 140 and 141 are located in cell A2 of the preparation tray. The medication identification system identifies medication 142 and validates that it corresponds to the prescription associated with box A1. In the same way, the medication identification system identifies medications 140 and 141, and validates that they correspond to the prescription associated with cell A2. Once validation is complete, the drawer is retracted to allow the medications to pass into the corresponding cells of the pill box 110. The drawer may be refracted automatically. The drawer may be refracted by a user.

In reference to FIG. 6B, we see a top view of the pill box 110 of FIG. 6A after the drawer has been refracted. As a result, medication 142 is located in cell A1 of the pill box and medications 140 and 141 are located in cell A2 of the pill box.

In reference to FIG. 7A, a connection device 132 includes several orifices 134. The connection device may be a reduction unit. FIG. 7B shows the connection device 132 in upside down position. The connection device 132 has an upper side and a lower side. The upper side [has] a number of orifices 134. The lower side has orifices 136. Each orifice 134 of the upper side corresponds to an orifice 136 of the lower side. For example, there are passages inside the reduction unit, which allows each orifice 134 of the upper side to communicate directly with an orifice 136 of the lower side. For example, when a medication arrives at an orifice 134, the medication passes through a passage to exit via an orifice 136.

In reference to FIG. 8A, a connection device 142 includes a number of orifices 144. FIG. 8B shows the connection device 142 in upside down position. The passages of the orifices 144 are more sloped, which reduces the total surface area of the lower side of the connection device 142.

The connection device is a connection device that can be connected to the preparation tray and to a pill box. The upper side of the connection device can be connected to the preparation tray. The lower side of the connection device can be connected to a pill box. In one configuration, the reduction unit can be connected to the preparation tray and comprises the same number of orifices as compartments or a larger number of orifices than the number of compartments of the preparation tray. The connection device can be connected to a pill box and comprises the same number of orifices as cells or a larger number of orifices than the number of cells of the pill box.

In reference to FIG. 7A, the orifices 134 are sized to correspond to the compartments 128 of the preparation tray 126. For example, the connection device 132 is going to be positioned below the preparation tray 126. Each compartment 128 of the preparation tray 126 has a surface with a length and a width. The surface allows for depositing medications. When the connection device 132 is positioned below the preparation tray 126, the surface of each orifice 134 of the reduction unit corresponds to the surface of each compartment 128.

In reference to FIGS. 3A and 4A, the surface 148 of the compartment of the preparation tray is larger than the surface 149 of the cell of the pill box, for example shown in FIG. 5B. Thus, in one configuration, the lower surface 148 of the compartment is larger than a lower surface of the cell 149 of the pill box. In the same way, the internal volume defined by the compartment is larger than the internal volume defined by the cell of the pill box.

The connection device allows the passage of one or more medications from a compartment of a second dispenser to its opposite compartment in a first dispenser. For example, the connection device allows the passage of one or more medications from a preparation tray to a pill box. The passage may take place via gravity.

In reference to FIG. 6A, we see a connection device 132 positioned below the preparation tray 126. For example, when the drawer 121 is refracted, the medications that are in the preparation tray are going to descend into the orifices of the connection device. Then, the medications are going to be located in the corresponding cell of the pill box, as shown in FIG. 6B.

Steps for Implementing the Method of Use
1. A blister card medication dispenser to be filled is placed in the holder;
2. Based on the prescription, the medications are positioned by the technician on the tray in the corresponding cells of the tray;
3. The medications placed on the tray are counted and verified by the optical scanning system as described in the EyeCon$^e$ system marketed by Avery Weigh-Tronix;
4. Validation of the content by the verification system compared to the prescription;
5. Opening of the retractable drawer by the operator;
6. The medications positioned on the tray fall via gravity into the corresponding cells of the blister pack following the path of the tubes; and Rectified Sheet (Rule 91.1)

7. The blister card medication dispenser is closed with a sealing sheet by the operator, then removed from the holder.

An identification and validation system for medications deposited, according to a prescription, in the compartments of a dispenser comprising n compartments, n being an integer greater than or equal to 1, each of the medications being able to be at least partially superimposed with at least one other medication present in the same compartment of the dispenser, said system includes:
a measuring device for gathering identifying characteristics of the medications deposited in each of the compartments of the dispenser;
a transmission device configured to transfer, to a calculation unit, the identifying characteristics gathered by the measuring device;
a calculation unit configured to determine, from the identifying characteristics gathered whether or not each of the medications effectively present in each of the compartments corresponds to a medication that, according to the prescription, should be present there and/or to indicate which compartment contains the non-correspondence(s) and/or what the nature of the non-correspondence(s) is.

The identification and validation system may include:
a measuring device configured to gather, separately or by packets, and potentially to analyze the identifying characteristics of the medications deposited in each of the compartments of the dispenser:
whether one of the medications present in a compartment is separated or not, by an empty space, from one of more neighboring medications and/or
whether one of the medications is resting against and/or partially or totally overlapping one or more adjacent medication(s);
a transmission device configured to transfer, to a calculation unit, the identifying characteristics gathered by the measuring device, analyzed or not analyzed or partially analyzed;
a calculation unit configured to:
isolate and/or analyze the identifying characteristics received from the transmission device for each of the medications effectively present in a compartment of the dispenser, and identify each of these medications,
i.—compare the characteristics isolated and/or analyzed in the preceding step with the information contained in a database, internal to the calculation unit or external to it, of the characteristics of the medications that are, according to the prescription, to be present in one of the compartments of the dispenser.

The identification and validation system being configured to determine whether or not:
all the medications effectively present in each of the compartments corresponds or not to those that, according to the prescription, should be present there; and/or
the number of medications effectively present in a compartment corresponds to the number of medications that should, according to the prescription, be present there; and/or
the total number of medications present in all the compartments of the dispenser corresponds to the total number of medications that should, according to the prescription, be present in the dispenser; and/or
the weight of the medications present in a compartment corresponds to the weight of the medications that should, according to the prescription, be present there and/or
the weight of all the medications present in all the compartments of the dispenser corresponds to the total weight of all the medications that, according to the prescription, should be present there.

The identifying characteristics of the medications are: geometric characteristics such as hidden shapes, partially hidden shapes or complete shapes, size, color, dimensions or texture, or one or more markings and luminescence. The measuring device includes at least one sensor and, preferably, includes several sensors positioned in a same plane or in staggered planes. The sensors are, compared to the plan in which the dispenser is positioned, positioned: above; below and/or laterally. At least one of the sensors may be moved to different positions in space. The dispenser has an at least partially flexible and/or pliable structure making it possible to distort the dispenser at least partially, and if necessary The measuring device is at least one chemical and/or physical analysis device preferably chosen from the group consisting of the following means:
a 2D visible light sensor (photo or video);
a 3D visible light sensor (photo or video);
an X-ray apparatus, as described more particularly in one of the following documents whose entire content is incorporated by reference in this application;
an RGB decomposition apparatus, as described more particularly in one of the following documents whose entire content is incorporated by reference in this application;
a color analyzer with illumination by different colored lighting including white light, ultraviolet light, red light, green light, blue light and/or infrared light, stroboscopic light;
an optical character recognition (OCR) and/or optical character verification (OCV) apparatus, as described more particularly in one of the following documents whose entire content is incorporated by reference in this application;
a spectroscope (near infrared or fluorescence) as described more particularly in one of the following documents whose entire content is incorporated by reference in this application;

an MMS (multimodal multiplex sampling) spectroscope as described more particularly in one of the following documents whose entire content is incorporated by reference in this application;
a magnetic resonance imaging device;
an ultrasound device;
a laser excitation scanner; and
a precision weighing device.

The first and the second dispenser comprise the same number of compartments. The first and the second dispenser each comprise a number of compartments that is advantageously between 7 and 28. The measuring device is an optical scanning system as described in the EyeCon® system marketed by the company Avery Weigh-Tronix. The medication identification and validation system is used to reduce the risk of error when filling a medication dispenser according to a prescription.

A method for validating the conformity, to a medical prescription, of the filling of a medication dispenser, the method includes the following steps:
   filling, according to a prescription, of the compartments of a dispenser, by an operator and/or by an automaton;
   determination, thanks to the use of at least one of the identification systems, of the content of each of the compartments; and
   sending of an error message and/or potential correction message concerning the content of one or more compartment(s) of the dispenser in case of non-conformity established by this system compared to the medical prescription.

The content of each of the compartments is determined thanks to the use of an identification system and the corresponding measurements are taken by sector of the container, and each sector may include one or more compartments.

A method for validating the conformity to a prescription, in which the content of each of the compartments is determined by means of the identification system and the corresponding measurements are taken after at least partial folding of a sector of the container, the folding being done advantageously along the line separating rows of compartments, the corresponding separation line preferably being produced from a flexible material and/or from a material that can become supple, particularly by thermal heating.

A multi-stage identification and validation system for medications deposited, according to a prescription, in the compartments of a dispenser intended for a patient and/or intended for a patient caregiver, said medications being able to be at least partially superimposed and/or resting against at least one other medication present in the same compartment of the dispenser, the system comprises:
   a first dispenser intended for the patient and/or for a patient caregiver;
   a second oversized dispenser (compared to the size of the first dispenser) comprising the same number of compartments or a number of compartments greater than the number of compartments of the first dispenser, this second dispenser preferably being large enough to prevent the stacking of the medications, and preferably positioned higher than the first dispenser, and advantageously above and/or offset;
   a connection device between the compartments of the first dispenser and those of the second dispenser, said connection device allowing the movement, preferably via gravity, of one or more medications from a compartment of the second dispenser to its opposite compartment in the first dispenser, said connection device preferably consisting of a bundle of conduits, which are preferably more or less parallel, each of the conduits being:
      in its upper part united with the lower part of one of the compartments of the second dispenser, and
      in its lower part united with the upper part of the compartment opposite it in the first dispenser;

The lower part of a compartment of the oversized second dispenser is configured to have a release device allowing, on demand, the medications of at least one of the compartments of the second dispenser to migrate to the opposite compartment of the first dispenser, and the upper opening of a conduit of the connection device is preferably larger than the lower orifice of the connection conduit;
   a measuring device configured to analyze the identifying characteristics of the medications deposited so that they do not overlap in each of the compartments of the oversized dispenser: whether one of the medications present in a compartment is separated by a space from one or more neighboring medications or is in contact with one or more adjacent medications;
   a transmission device configured to transfer the identifying characteristics (analyzed or not analyzed) gathered by the measuring device and relating to the medications present in the compartments of the second dispenser, to a calculation unit;
   a calculation unit configured to:
   isolate the identifying characteristics received from the transmission device for each of the medications effectively present in a compartment of the second dispenser, and identify each of these medications,
   compare the characteristics isolated in the preceding step with the information contained in a database of the characteristics of the medications that, according to the prescription, should be present in one of the compartments of the dispenser, and this identification and validation system sending a message according to which: all the medications effectively present in each of the compartments of the second dispenser correspond or not to those that, according to the prescription, should be present there;
      i. the number of medications effectively present in a compartment corresponds to the number of medications that should, according to the prescription, be present; and/or
   the total number of medications present in all the compartments of the dispenser corresponds to the total number of medications that should, according to the prescription, be in the dispenser; and/or
   the weight of all the medications present in a compartment corresponds to the weight of the medications that should, according to the prescription, be present and/or the weight of all the medications present in all the compartments of the dispenser corresponds to the total weight of all the medications that, according to the prescription, should be present there.

A method for producing the multi-stage identification and validation system through the use of at least one of the known assembly techniques such as: screwing, gluing, bolting, dovetailing, riveting and welding.

The medication identification and validation system is used to reduce the risk of error when filling a medication dispenser according to a prescription.

A method for validating the conformity to a medical prescription, of the filling of a medication dispenser, said method includes the following steps: filling according to a medical prescription of the compartments of an oversized dispenser;
  determination of the content of each of the compartments of the oversized system thanks to the use of at least one of the identification and/or measuring systems according to this disclosure; and/or
  sending of a message of non (sic) non-conformity established compared to the medical prescription; and/or
  potential correction of the content of one of the compartments of the dispenser in case of established non-conformity compared to the medical prescription; and
  passage of the medications present in a compartment of the oversized dispenser into the opposite compartment of a standard size dispenser.

The content of each of the compartments is determined thanks to the use of one of the multi-stage identification systems as defined in this disclosure, and the corresponding measurements are taken by sector of the container.

The content of each of the compartments is determined thanks to the use of one of the multi-stage identification systems and the corresponding measurements are taken with at least partial folding of a sector of the container.

Equipment for checking the conformity of the content of a medication dispenser to a prescription, consists of:
  a first and a second medication dispenser, the second dispenser being oversized compared to the first dispenser;
  a connection device between the compartments of the first dispenser and those of the second dispenser, said device allowing the movement, preferably via gravity, of one or more medications from a compartment of the second oversized dispenser to its opposite compartment in the first dispenser, said connection device preferably consisting of a bundle of conduits with each of the conduits of the bundle being:
  in its upper part united with the lower part of one of the compartments of the second oversized dispenser, and
    i.—in its lower part united with the upper part of a compartment of the first dispenser opposite it,
the lower part of a compartment of the oversized dispenser being configured to have a release device allowing, on demand, the medications of at least one of the compartments of the second dispenser to migrate to the opposite compartment of the first dispenser, and the upper opening of a connection conduit preferably being larger than the lower orifice of the connection conduit.

The conformity assessment equipment is a sliding plate of the floor of the compartments of the oversized dispenser and the sliding plate can move horizontally in parallel grooves situated in the extension of the side walls of 2. The conduits of the bundle of conduits are made of a supple and/or deformable material that is preferably an at least partially transparent material. The size of the second oversized dispenser is 1.5 to 3.5 times the size of the first dispenser. The distance between the lower part of the second oversized dispenser and the upper part of the first dispenser is between 10 and 60 cm.

A method for producing assessment equipment through the use of at least one of the known assembly techniques such as: screwing, gluing, bolting, dovetailing, riveting and welding.

The use of the assessment equipment to reduce the risk of error when filling a medication dispenser according to a prescription.

A method for validating the conformity to a medical prescription, of the filling of a medication dispenser integrated in conformity assessment equipment, said method includes the following steps:
  filling of the compartments of an oversized dispenser according to a medical prescription;
  determination of the content of each of the compartments of the oversized dispenser;
  potential correction of the content of one of the compartments of the oversized dispenser in case of established non-conformity compared to the medical prescription; and
  transfer of the medications present in a compartment of the oversized dispenser into the opposite compartment of the first dispenser.

Summary of the advantages offered by the medication identification and validation systems according to this disclosure, particularly the possibilities of:
  verification of all of the compartments of the medication dispenser; verification of the overlapping medications in the compartment or compartments;
  integration in the work procedures of pharmacies for the dispensing of prescriptions to the patient; and
  complementarity of the work methods of pharmacists for inspecting and verifying the medication dispensers produced by the technical assistants.

Summary of the advantages of the multi-stage medication identification and validation systems according to this disclosure, particularly the possibilities of:
  verifying all of the medications that will be deposited in the compartments of the medication dispenser;
  no possibility of overlapping of the medications present in a same compartment, which limits the calculation and equipment requirements for faultless medication inspection and verification;
  integration in the work procedures of pharmacies for the dispensing of prescriptions to the patient and complementary to the work methods of pharmacists for inspecting and verifying the medication dispensers produced by the technical assistants; and
  in case of power outage and manual operation, inspection and verification of medications remains possible and is facilitated by the positioning of the oversized tray.

This disclosure is not limited to an identification of medications through optical recognition alone, but may include another method or apparatus for completing this recognition such as a laser or spectrometer.

Although this disclosure has been described by means of specific implementations, it is understood that a number of variations and modifications may be added to these implementations, and this disclosure aims to cover such modifications, uses or adaptations of this disclosure, in general, according to the principles of the disclosure and including any variation of this description that becomes known or conventional in the field of activity of this disclosure, and that can be applied to the essential elements mentioned above, in accordance with the scope of the following claims.

The invention claimed is:

1. A stage system for identifying and validating drugs disposed, according to a prescription, in the compartments of a dispenser for a patient and/or for a person accompanying the patient, said system comprising:
  a first dispenser for the patient and/or for a person accompanying the patient;
  a second dispenser oversized compared to the size of the first dispenser, including the same number of compartments or a number of compartments greater than the number of compartments of the first dispenser;

a connection device between the compartments of the first dispenser and those of the second dispenser, said connection device allowing the transit of one or several drugs, from one compartment of the second dispenser towards its opposite of the first dispenser, the lower part of a compartment of the second dispenser being configured so as to have a releasing device letting, on request, the drugs of one of the compartments of the second dispenser migrate to the opposite compartment of the first dispenser;

a measuring device configured to collect and analyze drug identification characteristics, the drugs being disposed so as not to overlap, in each of the compartments of the second dispenser: whether one of the drugs present in one compartment is separated by a space from one or several neighboring drugs or whether it is in contact with one or several adjacent drug(s);

a transmission device configured to transfer the analyzed or non-analyzed identification characteristics collected by the measuring device and relating to the drugs present in the compartments of the second dispenser, to a computation unit; and the computation unit being configured to:

isolate the identification characteristics received from the transmission device for each of the drugs actually present in one compartment of the second dispenser, and identify each of these drugs, compare the identification characteristics that have been isolated with the information contained in a database of the characteristics of the drugs having to be present, according to the prescription, in one of the compartments of the second dispenser, and said identification and validation system being configured to emit a message according to which:

all the drugs actually present in each of the compartments of the second dispenser correspond or not to those that, according to the prescription, should be there;

the number of drugs actually present in one compartment corresponds to the number of drugs that, according to the prescription, should be there;

the total number of drugs present in all the compartments of the second dispenser corresponds to the total number of drugs that, according to the prescription, should be in the second dispenser;

the weight of the drugs present in one compartment corresponds to the weight of the drugs that, according to the prescription, should be there; and/or the weight of all the drugs present in all the compartments of the second dispenser corresponds to the total weight of all the drugs that, according to the prescription, should be there.

2. The system according to claim 1, said system having at least one of the following characteristics:

the drugs are at least partially superimposed and/or alongside at least another drug present in the same compartment of the second dispenser;

said second dispenser being of sufficient size to avoid the overlapping of drugs;

said second dispenser being positioned at a greater height than the first dispenser;

said second dispenser being positioned and advantageously above and/or offset;

said connection device allowing transit by gravity of one or several drugs from one compartment of the second dispenser towards its opposite of the first dispenser;— the connection device consisting of a bundle of conduits that are preferably substantially parallel; and the upper opening of a conduit of the connection device being larger than the lower orifice of the connection conduit.

3. The system, according to claim 1, wherein the first and the second dispenser comprise the same even number of compartments.

4. The system according to claim 3, wherein the first and the second dispenser comprise an even number of compartments varying from 7 to 28.

5. The system, according to claim 1, wherein the releasing device is a sliding plate constituting the floor of the compartments of the second dispenser, the sliding plate can move horizontally in parallel grooves located in the extension of the side walls by 2.

6. The system according to claim 2, wherein the conduits of the bundle of conduits are made of a flexible and/or deformable material which is preferably an at least partially transparent material.

7. The system according to claim 1, wherein the size of the second dispenser is 1.5 to 3.5 times the size of the first dispenser.

8. The system according to claim 1, wherein the distance between the lower part of the second dispenser and the upper part of the first dispenser is comprised between 10 and 60 cm.

* * * * *